(12) United States Patent
Aceti et al.

(10) Patent No.: US 6,473,511 B1
(45) Date of Patent: *Oct. 29, 2002

(54) DISPOSABLE HEARING AID WITH INTEGRAL POWER SOURCE

(75) Inventors: John Gregory Aceti, Cranbury, NJ (US); Walter Paul Sjursen, Washington Crossing, PA (US); Marvin Allan Leedom, Princeton, NJ (US); Derek Mahoney, Manalapan, NJ (US); Fredrick Fritz, Skillman, NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/263,593

(22) Filed: Mar. 5, 1999

Related U.S. Application Data

(63) Continuation-in-part of application No. 08/815,852, filed on Mar. 12, 1997, now Pat. No. 5,881,159.

(51) Int. Cl.[7] ................................................ H04R 25/00
(52) U.S. Cl. ........................ 381/322; 381/323; 381/328
(58) Field of Search ................................ 381/312, 322, 381/323, 324, 328, 329; 429/27, 72, 86, 89, 96, 100, 110, 49

(56) References Cited

U.S. PATENT DOCUMENTS

| | | | |
|---|---|---|---|
| 3,527,901 A | | 9/1970 | Geib |
| 3,598,928 A | | 8/1971 | Hickox |
| 3,783,201 A | | 1/1974 | Weiss |
| 4,262,062 A | * | 4/1981 | Zatsky ........................ 429/27 |
| 4,379,988 A | * | 4/1983 | Mattatall .................... 381/323 |
| 4,539,440 A | | 9/1985 | Sciarra |
| 4,639,556 A | | 1/1987 | Hartl et al. |
| 4,712,245 A | * | 12/1987 | Lyregaard .................. 381/328 |
| 4,716,985 A | | 1/1988 | Haertl |
| 4,870,688 A | | 9/1989 | Voroba et al. |
| 4,969,534 A | | 11/1990 | Kolpe et al. |
| 5,002,151 A | | 3/1991 | Oliveira et al. |
| 5,012,520 A | | 4/1991 | Steegar |
| 5,133,016 A | * | 7/1992 | Clark .......................... 381/322 |
| 5,141,455 A | | 8/1992 | Ponn |

(List continued on next page.)

FOREIGN PATENT DOCUMENTS

| | | |
|---|---|---|
| WO | WO 97/34443 | 9/1997 |
| WO | WO 97/36456 | 10/1997 |

*Primary Examiner*—Melur Ramakrishnaiah
*Assistant Examiner*—Suhan Ni
(74) *Attorney, Agent, or Firm*—Hamilton, Brook, Smith & Reynolds, P.C.

(57) ABSTRACT

A hearing aid includes a microphone, signal processing circuitry, receiver and integral battery all mounted in a casing. The battery may be a metal-air device. The battery may be activated by removing a tape which blocks air holes on the battery or, if the battery is sealed into the hearing aid, air-vent holes on the hearing aid. The hearing aid may also include an air-blocking mechanism which is activated when the hearing aid is inserted in the user's ear and deactivated when the hearing aid is removed. The assembled hearing aid may also be packaged in non-permeable packaging material to extinguish battery activity. The hearing aid may also include an electronic switch which monitors the battery potential to disconnect the battery from the hearing aid electronics when the battery is deprived of oxygen and which connects the battery to the electronics when oxygen is provided to the battery. In one embodiment of the invention, the integral battery is a rechargeable battery which is recharged via external contacts. In another embodiment, the battery is recharged using an induced alternating current potential which is rectified before being applied to the battery.

14 Claims, 7 Drawing Sheets

U.S. PATENT DOCUMENTS

| | | | |
|---|---|---|---|
| 5,146,051 A | | 9/1992 | Hermann |
| 5,185,802 A | | 2/1993 | Stanton |
| 5,187,746 A | * | 2/1993 | Narisawa .................... 381/322 |
| 5,210,804 A | * | 5/1993 | Schmid ...................... 381/323 |
| 5,249,234 A | * | 9/1993 | Butler ........................ 381/322 |
| 5,405,713 A | * | 4/1995 | Pecherer et al. ............... 429/49 |
| 5,724,431 A | * | 3/1998 | Reiter et al. ................. 381/322 |
| 5,881,159 A | * | 3/1999 | Aceti et al. .................. 381/322 |
| 5,949,895 A | * | 9/1999 | Ball et al. .................... 381/322 |
| 6,041,128 A | * | 3/2000 | Narisawa et al. ........... 381/322 |

* cited by examiner

30-DAY

3-DAY

DISPOSABLE HEARING AID WITH INTEGRAL POWER SOURCE

This is a continuation-in-part of applicant Ser. No. 08/815,852 filed Mar. 12, 1997 now U.S. Pat. No. 5,881,159.

FIELD OF THE INVENTION

The present invention is directed to a hearing aid, and, more particularly to a hearing aid with a non-removable power source that is small and inexpensive so as to be disposable.

BACKGROUND OF THE INVENTION

Modern hearing aids comprise an earmold having therein the necessary electronics for amplifying and otherwise conditioning sound to compensate for a user's hearing loss. Such electronics generally include a microphone for receiving the sound and converting the sound to an electrical signal, an electronic circuit for amplifying and processing the signal produced by the microphone, a speaker (also known as a receiver) for converting the processed signals into sound energy and a battery for providing operational power to the hearing aid. The earmold is generally made of a hard plastic, and is specially designed and molded to fill the ear of the person who is to use the hearing aid. The earmold is made of a hard plastic so as to have a long life and so that it can be periodically cleaned. The electronics of the signal processing circuitry are generally adjusted to meet its users specific hearing requirements. These requirements are obtained by first testing the user's hearing and then designing a circuit having a frequency response characteristic that compensates for any hearing loss discovered in the test. After the desired circuit is determined from the tests, it may be finally adjusted by a hearing aid specialist to meet the final requirements of the party. All of the above features of the structure of the hearing aid, the method of making it and the method of adjusting it make the hearing aid relatively expensive.

In addition, hearing aids have a battery that must be replaced periodically as it is small and has only a limited lifetime of operation. Hearing aid users frequently complain about the difficulty in replacing batteries. Batteries are becoming increasingly difficult to handle as hearing aids and batteries become smaller. It is especially difficult for the majority of hearing aid wearers who are over 65 years of age and who are losing visual and motor abilities. Having a hearing aid that does not require battery replacement would be advantageous to these users.

In addition to the replacement of the battery, the hearing aid must be removed from the ear periodically to be cleaned of earwax and other contaminants. While a user may be able to clean the surfaces of the hearing aid, contaminants which enter into the hearing aid mechanism must be cleaned professionally. This adds to the cost of operating the hearing aid.

A possible solution to this problem is to provide a disposable hearing aid, as is disclosed in co-pending patent application Ser. No. 80/815,852 entitled "DISPOSABLE HEARING AID." One difficulty with a disposable hearing aid, however, is that its permanent battery may discharge during the shelf-life period. To ensure that the hearing aid lasts for its target life of 30 days, for example, a switch may be included in the device to keep the battery from discharging. Two types of switches may be used: an on/off switch or an on-only switch. An on-only switch may be used to activate the device once. Once put into service the device remains on until the battery is depleted. An on/off switch, in addition to activating the device once, may allow the hearing aid to be turned off during non-use periods, for example at sleep time.

It would be desirable to have a disposable hearing aid which is inexpensive with regard to both the structure of the parts of the hearing aid and its method of making and packaging, and which can be easily used by the person, particularly the elderly.

SUMMARY OF THE INVENTION

The present invention is directed to a hearing aid having an integral power source. The integral power source is for example, non-replaceable or non-removeable. The hearing aid includes a circuit for receiving and amplifying the sound, and a shell surrounding the circuit. An earmold of a soft, pliable material surrounds the shell and is adapted to fit into and mold to the ear of a person.

The present invention is also directed to a hearing aid with a non-replaceable rechargeable power source.

In another embodiment, the present invention provides a switch which is automatically engaged when the hearing aid is inserted into the ear and automatically disengaged when the hearing aid is removed from the ear.

In still another embodiment, the present invention provides an on/off switch for controlling power in a hearing aid, which receives operational power from a metal air battery. The switch includes a mechanical structure which selectively prevents air from entering the battery and electronic components which detect when the battery is operating without air to disconnect the battery from the hearing aid circuitry.

In still another embodiment, the present invention provides means for packaging the hearing aid to enhance life expectancy of the battery.

It is understood that the foregoing general description and the following detailed description are exemplary, but not restrictive, of the invention.

BRIEF DESCRIPTION OF THE DRAWINGS

The invention is best understood from the following detailed description when read in connection with the accompanying drawing. Included in the drawing are the following figures.

DETAILED DESCRIPTION

Figure 1:
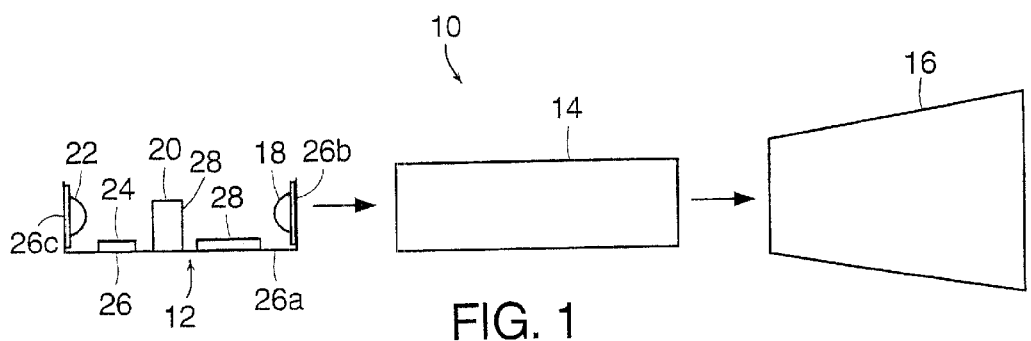
FIG. 1 is an exploded schematic view of a first embodiment of a hearing aid according to the present invention.
Figure 2:
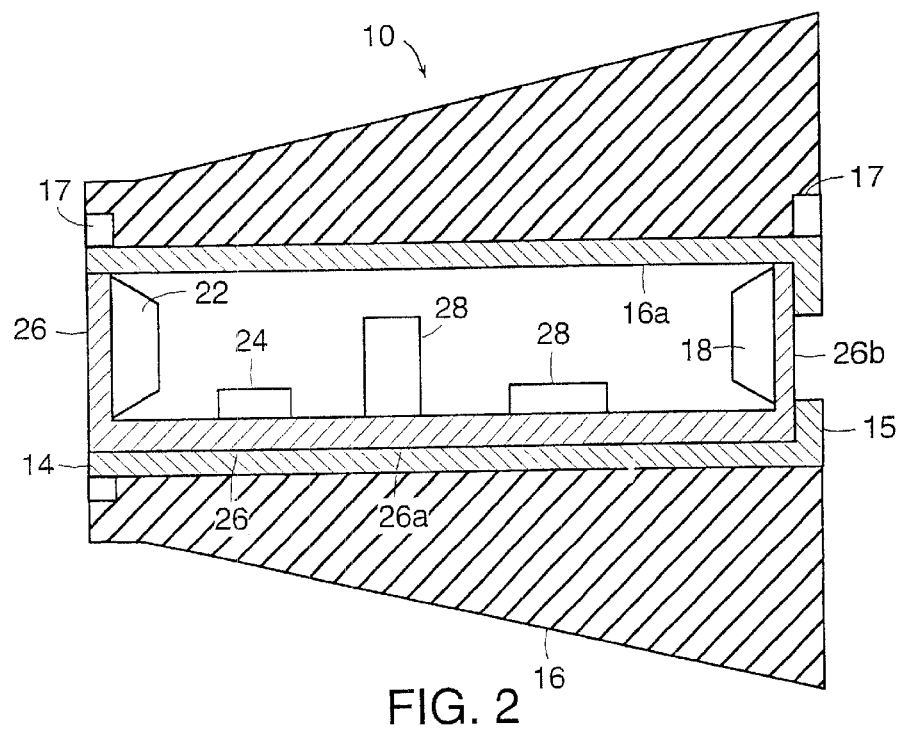
FIG. 2 is a sectional view of the assembled hearing aid shown in FIG. 1.
Figure 3:
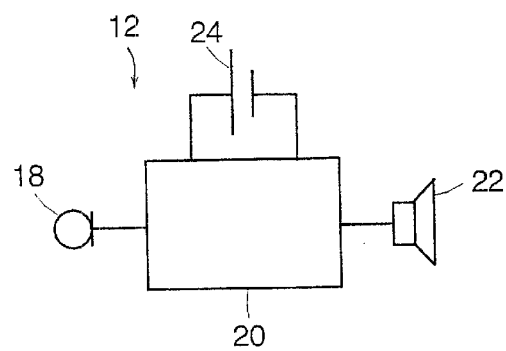
FIG. 3 is a schematic diagram, partly in block diagram form, of the components of a hearing aid according to the present invention.

Referring initially to FIGS. 1 and 2 of the drawings, the hearing aid of the present invention is generally designated as 10. Hearing aid 10 comprises an electronics assembly 12, a shell 14 and an earmold 16. As shown in FIG. 3, the electronics assembly 12 includes a microphone 18, which is adapted to receive the sound and convert the sound into electrical signals. The microphone 18 is connected to the input of a signal processing circuitry 20 which amplifies the sound, diminishes any undesirable background noise and which can adjust the sound according to the particular needs of the hearing of the user. The output of the signal processing circuitry is connected to a receiver 22 which converts the output signals to sound and directs the sound into the ear of the user. A suitable battery 24 of any desired structure is connected to the signal processing circuitry 20 to operate the circuitry 20.

As shown in FIGS. 1 and 2, the electronics assembly 12 includes a flexible printed circuit 26 having a base 26a and upright arms 26b and 26c at its ends. The flexible printed circuit 26 also includes therein paths of a conductive metal (not shown). The microphone 18 is mounted on the upright arm 26b at one end of the printed circuit 26, and the receiver 22 is mounted on the upright arm 26c at the other end of the printed circuit 26. The components 28 of the signal processing circuitry 20 and the battery 24 are mounted on the base 26a of the printed circuit 26 between its ends. The microphone 18 can be any very small microphone, which is presently on the market or can be a silicon microphone in which the diaphragm of the microphone 18 is a thin layer of silicon.

The signal processing circuitry 20 can be of any well-known type, which will provide the desired amplification. For a very short operating hearing aid 10, such as for a three-day operation, the signal processing circuitry 20 can be of the type, which will provide amplification with fixed gain and frequency response. A simple, low-cost class-A amplifier can be used. For a longer lasting hearing aid 10, such as a 30-day device, the signal processing circuitry 20 can be of the type, which contains a two-channel amplifier with signal compression. One channel can process the lower frequency spectrum while the other channel can process the higher frequency spectrum. To extend battery life, a more efficient class-D output amplifier can be used. For any type of signal processing circuitry 20, integrated circuits that perform the required signal processing should be used and are readily available. To achieve the different responses, different values of passive components, such as resistors and capacitors, can be used. The speaker 22 can be of any type of small speaker readily available. The battery 24 can be of any small type having sufficient power and voltage to operate the signal processing circuitry used.

The shell 14 can be, for example, a flexible hollow cylindrical element that is adapted to house and protect the electronics assembly 12. The shell 14 is of a molded, flexible plastic material and contains means, such as ribs 15 shown in FIG. 2, to orient and retain the electronics assembly 12 therein. The shell 14 is of a material, which protects the electronics assembly 12 from moisture and mechanical damage. The shell 14 also provides acoustical features for facilitating incoming and outgoing sound, and has external features, such as ribs 17, which help retain it in the earmold 16.

Earmold 16 is of a soft, durable and compliant material. It can be of a cold-cured methacrylate, heat-cured methacrylate, heat-cured silicone, polyvinyl chloride copolymer or polyethylene co-polymer. The earmold 16 has an inner opening 16a into which the shell 14 containing the electronics assembly 12 is inserted and retained. The outer configuration of the earmold 16, such as its shape and size, is such that it can be readily inserted in the ear canal of the user and which will flexibly mold itself to the shape of the ear canal. Since the earmold 16 is of a compliant material, the pressure of the earmold 16 against the wall of the ear channel produces a good fit needed to prevent feedback and to help retain the hearing aid 10 in the ear. It has been found that earmolds of soft material are superior to those of hard material in the attenuation of feedback acoustics, improved comfort and reduced irritation.

Figure 4:
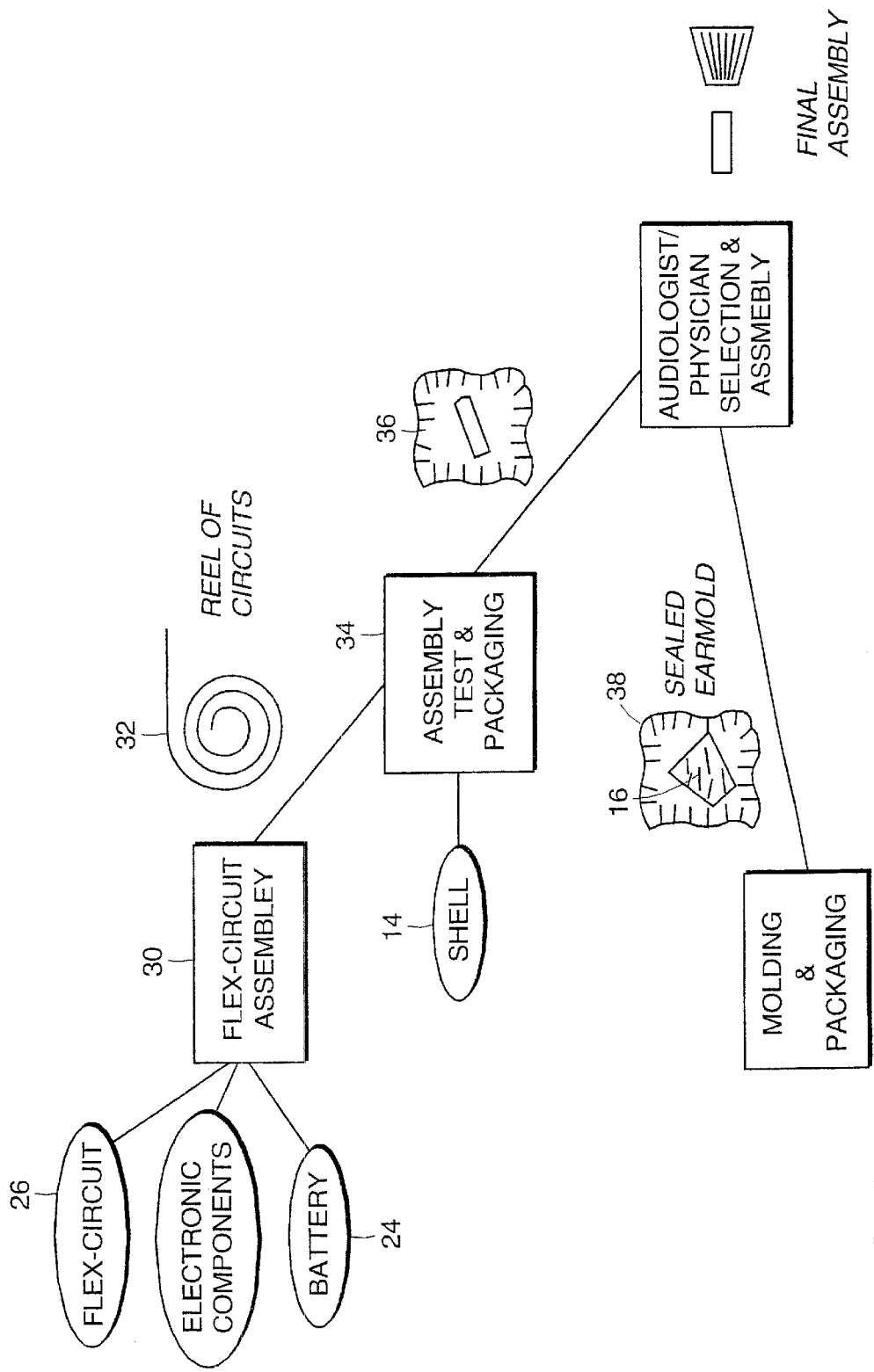
FIG. 4 is a flow chart diagram showing a method of assembling the hearing aid of the present invention.

Referring to FIG. 4, there is illustrated a method of assembling the hearing aid 10 of the present invention. A flexible circuit 26 is fed from a reel along with the various components 28, which make up the assembly 12. Including microphones 18, receivers 22 and batteries 24, into an assembly apparatus 30. The assembly apparatus 30 assembles the components onto the flexible circuit to form a strip containing a plurality of the hearing aid electronics assemblies 12. The completed assemblies are mounted on a reel to form a reel 32 of the hearing aid component assemblies.

The flexible circuit assemblies of the reel 32 are then fed along with shells 14 into an assembler 34 where the electronics assemblies 12 are cut apart from the reel, and each electronics assembly 12 is formed and inserted into a shell 14. The shell assembly may then be inserted into a package 36, which is hermetically sealed and contains a gas, that protects the shell assembly from the atmosphere and extinguishes battery activity.

The earmolds 16 are molded in a suitable molding apparatus and may also be packaged in hermetically sealed packages 38. The earmolds 16 are preferably molded in a few different sizes so that a suitable size can be used for each user of the hearing aid 10. Because the earmolds are formed from a compliant material one size of earmold may be appropriate for a number of different ear configurations.

Figure 5B:
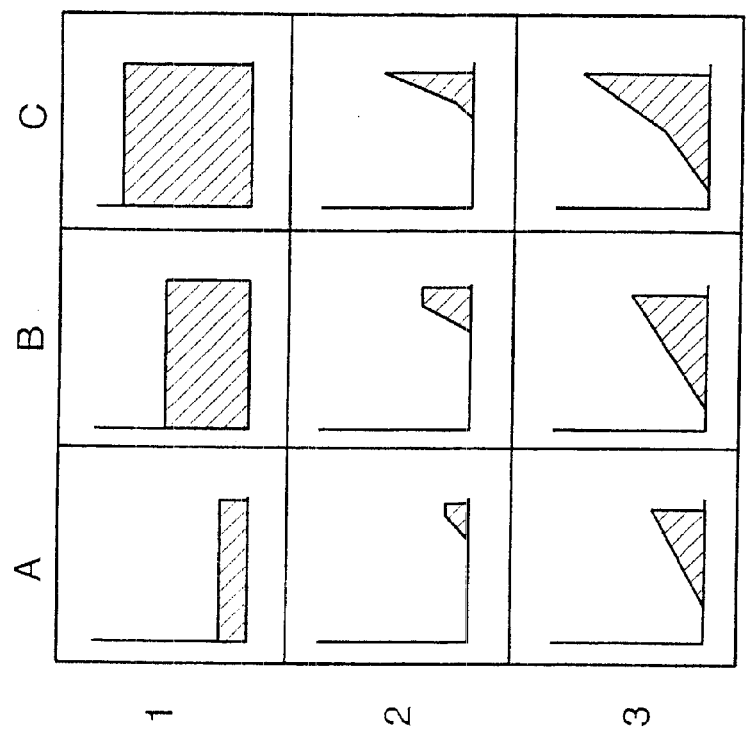
FIGS. 5a and 5b are charts showing the various responses of the amplifier circuit which can be used in a hearing aid according to the present invention.
Figure 5A:
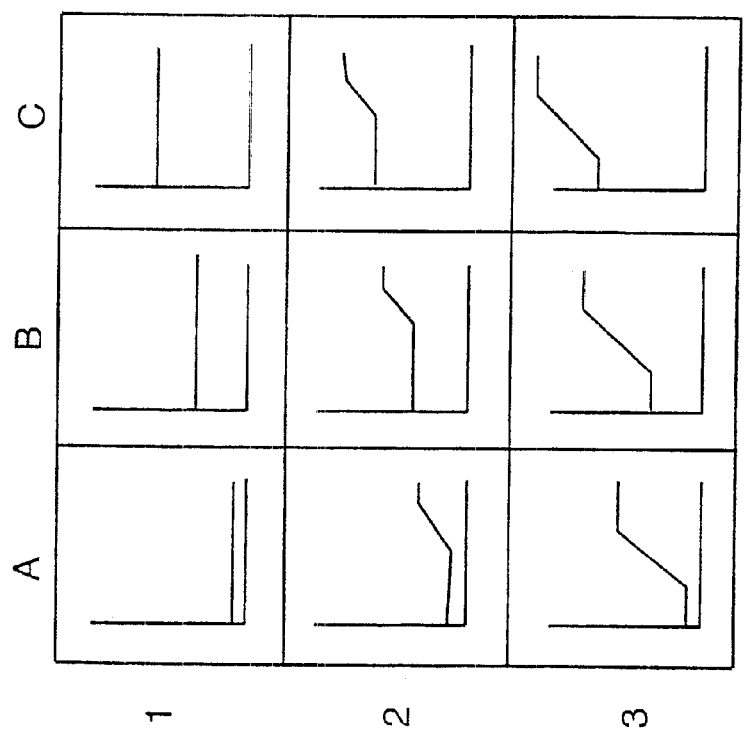

The signal processing circuitry 20 of the electronics assembly 12 may be designed, for example, to accommodate high-frequency hearing losses and flat-frequency hearing losses in the mild to moderate ranges. The signal processing circuitry 20 for different electronics assemblies 12 may be made to provide different audiological responses. FIGS. 5a and 5b are charts showing the various responses which may be provided by the different electronics assemblies 12 which are made in the process of the present invention. FIG. 5a shows the responses for a three-day device which has a fixed gain and frequency response, and FIG. 5b shows the responses for a 30-day device which has a two-channel amplifier. In each of FIGS. 5a and 5b, the columns represent different amplifier gains with column A being the lowest gain and column C being the highest gain. The rows represent different frequency response characteristics with row 1 being a flat response, row 2 a mild high frequency boost and row 3 the moderate high frequency boost. Thus, in making the signal processing circuitry 20, different components may be used so as to make up a fixed number of circuits having different gains and frequency responses as shown in FIGS. 5a and 5b. The different circuits are marked according to the charts of FIGS. 5a and 5b according to gain and frequency response, such as A1, A2, A3, B1, etc.

The last step in making the hearing aid 10 of the present invention is done by an audiologist or physician after the hearing of the user is tested and it is determined what type of audiological response is required of the hearing aid. The audiologist or physician checks the charts shown in FIGS. 5a and 5b and picks the signal processing circuitry 20 which will provide the audiological response required by the user. The audiologist/physician then picks the shell assembly, which contains the desired electronics, and picks an earmold 16 of the appropriate size for the user. The shell assembly is then inserted into the earmold 16 and the hearing aid 10 is ready to be inserted in the ear of the user.

In a hearing aid 10 according to the present invention, the signal processing circuitry 20 has fixed audio characteristics and is made in a limited number of acoustical formats. In addition, the acoustical format is preprogrammed in the electronics manufacture so that no potentiometers or other adjustable devices are needed for tailor the device for a particular user. In addition, in this first embodiment of the invention, the units are used only for the life of the battery. Thus, no on/off switch is used. Therefore, it is of simple design having a minimum number of components and is easy to assemble on an automatic basis. The signal processing circuitry 20 and the entire electronics assembly 12 is inexpensive because it can be easily made in large volumes and achieve economies of scale. The assembly 12 is encased in a simple hollow shell, which is easy to assemble by automated methods. Also, the earmold 16 is of simple design and of a soft, pliable material so as to be inexpensive. Thus, the entire hearing aid 10 is of a minimum number of inexpensive parts and is easy to assemble so that the hearing aid 10 is relatively inexpensive compared with presently used hearing aids.

Because the hearing aid 10 is so inexpensive, it is disposable. Therefore, when the battery 24 of the hearing aid 10 is depleted, instead of replacing the battery 24, the whole hearing aid can be disposed of and replaced with a completely new hearing aid 10. Thus, there is provided by the present invention, a hearing aid 10 which is inexpensive to manufacture so as to be disposable. However, the hearing aid 10 still has all of the audio characteristics required by the user and has a high reliability. Furthermore, since the hearing aid of the present invention is small and has a soft, pliable earmold, it is more comfortable to wear. In addition, since it is disposable, it requires no service for major cleaning, repair and adjustment.

As set forth above, hearing aids commonly use metal-air batteries as a power source and in particular the zinc-air type of battery. Metal air batteries have the property that the oxygen in the air is the activator of the battery chemistry. As such, the battery is quiescent in the absence of air. Zinc-air cells are activated when air, and in particular oxygen, is allowed to enter the cell. In some zinc-air cells, a pull-tab covers one or more small openings that allow air to reach the air-cathode assembly. The pull-tab may be designed to allow air to diffuse slowly into the cell. With the pull-tab sealing the cell, the cell is oxygen deprived and may not support the same current as an unsealed cell.

The chemical reaction associated with an oxygen-enriched zinc-air cell is as follows:

cathode reaction $\frac{1}{2} O_2 + H_2O + 2e^- \rightarrow 2OH^-$ $E° = 0.40$ V anode reaction $Zn \rightarrow Zn^{2+} + 2e^-$ $E° = 1.25$ V $Zn^{2+} + 2OH^- \rightarrow Zn(OH)_2$ $Zn(OH)_2 \rightarrow ZnO + H_2O$ overall reaction $Zn + \frac{1}{2} O_2 \rightarrow ZnO$ $E° = 1.65$ V When a cell is completely deprived of oxygen, the cell becomes a zinc-hydroxide cell, wherein the cathode material is hydroxide taken from the electrolyte. The chemical reaction associated with the zinc-hydroxide cell is as follows:

cathode reaction $2H_2O + 2e^- \rightarrow H_2 + 2OH^-$ $E° = -0.828$ V anode reaction $Zn + 4OH^- \rightarrow ZnO_2^{-2} + 2H_2O + 2e^-$ $E° = 1.21$ V overall reaction $Zn + 2OH^- \rightarrow ZnO_2^{-2} + H_2$ $E° = 0.388$ V A pull-tab that is impermeable to oxygen may be used to seal the air openings. Instead of an oxygen impermeable pull-tab, or in addition to such a pull-tab, the cell (battery) may be sealed in a nitrogen-filled, oxygen impermeable bag. The relative humidity of the nitrogen gas within the bag may be, for example, between 40 and 60 percent so as not to dry out the cell. When the sealed bag is opened or the pull-tab is removed, oxygen diffuses into the cell, the cell reverts to a zinc-air cell, and the voltage may increase, for example, from about 0.39 volts to more than 1.4 volts.

Another embodiment of this invention includes a non-replaceable metal-air battery sealed within the hearing aid. Because the battery can not be replaced, it is not accessible by the user and is sealed within the product. Nevertheless, a means must be provided to allow airflow to the battery or the device will not work. In an exemplary disposable hearing aid shown in FIG. 6A, a passageway 64 is provided, such that air may travel through the outer shell of the hearing aid to the cathode side of the battery. The passageway is a sealed volume, such that when the outer holes are covered by a tape 59, no air is permitted to enter the passageway 64 and reach the air ingress holes 68 and into the cathode area 70 of the battery 24.

Traditional hearing aids do not have this air passageway, as the battery is always mounted in a leaky shell which permits air ingress. No allowance is made to control the flow of air or to terminate air ingress during shipment or storage.

During storage or shipment, the disposable hearing aid may be exposed to an uncontrolled environment. Metal-air batteries are sensitive in their performance and life expectancy to the environment. It is known by those skilled in the art of making metal-air batteries, that battery life is enhanced by minimizing exposure to $O_2$ or $CO_2$ during storage. Even when the battery is not coupled to a load, these gases may cause chemical reactions in the battery to degrade its life. It is therefore important to protect and seal the integrated battery in a disposable hearing aid from the environment. Traditional metal-air batteries use a non-permeable tape over air ingress holes to protect the battery.

To assure that the air passageways do not reach the cathode side of the battery during storage or shipment, this invention discloses four different means for sealing the battery:

1) sealing the battery with non-permeable tape applied to the air ingress holes on the cathode;
2) sealing the hearing aid with the non-permeable tape applied to air ingress holes on the faceplate; and
3) sealing the hearing aid with non-permeable packaging.
4) providing the hearing aid casing with a reclosable air-tight sealing device.

Figure 6A:
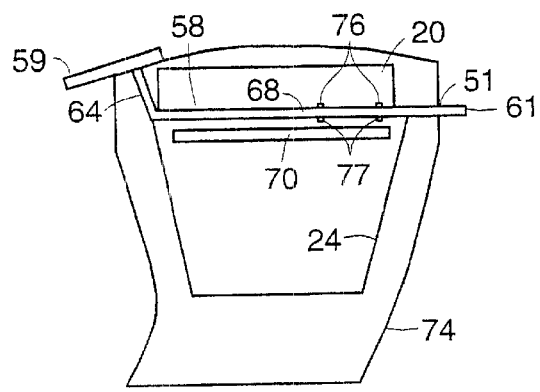
FIGS. 6a, 6b, and 6c are sectional views of an alternative embodiment of a hearing aid according to the present invention showing an ON/OFF air block switch.

The simplest and most direct means of sealing a battery in a disposable hearing aid is by applying a non-permeable tape 61 to the battery 24, directly covering the air ingress holes 68 as shown in FIG. 6A. A disposable hearing aid which uses this sealing strategy is designed with a slot 58 in the shell 74, such that a tab connected to the tape 61 on the battery 24 protrudes from the slot. When the user is ready to activate the unit, the tab is pulled from the unit exposing the battery's air ingress holes 68, activating the battery. This design also has the dual function of an ON only switch as described below.

U.S. Patent Application entitled "MODULAR ELECTRACOUSTIC INSTRUMENT" by Leedom et al., Ser. No. 09/250,572, which is incorporated herein by reference for its teaching on disposable hearing aids. The referenced application describes a hearing aid having a removable tab that is used to seal the battery prior to use. In the exemplary embodiment of the invention, the removable tab 61 is positioned between the conducting contacts 76 on the bottom of the signal processing section 20 and corresponding contacts 77 on the top of the casing of the battery 24 to disconnect the battery 24 from the signal processing circuitry 20 until the tab 61 is pulled. The removable tab substantially seals the vent 68 in the battery casing. When the tab is pulled, oxygen is supplied to the battery through the vent and the battery is electrically connected to the hearing aid circuitry. As set forth in the above-referenced patent to Leedom et al. one or both of the contacts 76 and 77 may be spring contacts which make an electrical connection after the tab 61 is removed.

An alternative to putting tape on the battery is to put tape 59 covering the air vent holes 64 of the hearing aid. As described above, a design feature of a disposable hearing aid according to the present invention provides for air passageways to allow air to travel into the battery. For this approach to work, the battery is desirably sealed in the hearing aid so that no air can get into the battery except through specific passageways. Every hearing aid has two passageways, a proximal passageway through which acoustic pressure waves interact with the microphone and a distal passageway through which the receiver produces acoustic pressure waves to activate the eardrum. In a hearing aid according to the present invention, the battery may be sealed from the air except for one of these passageways. The proximal passageway may be hermetically sealed to the battery or may be integrally molded to the faceplate so that the battery coming into contact with the faceplate forms a hermetic seal except for the proximal passageway.

Additionally, the distal passageway may be sealed to the battery with the use of a non-permeable adhesive or sealant. The proximal passageway 64 may be made from the housing material of the hearing aid (such as acrylic or Noryl) which connects the air holes in the faceplate with the air holes in the outer casing of the zinc air battery.

Alternatively, the hearing aid shell itself may form a hermetic seal around the electronics and battery as described below with reference to FIG. 6B. With this design no special passageway is required. Air may only enter the unit in a controlled manner through specific air ingress holes.

With either of the alternative designs, a non-permeable tape 59 may then be applied over the holes in the faceplate. When the user is ready to activate and use the product, the tape is simply removed.

Another alternative means of preventing air from degrading the battery while in storage is to use non-permeable packaging 38 (shown in FIG. 4) in lieu of a film tab on the battery or hearing aid. The following three materials are examples of such packaging:

1. Barex—made by Klockner-Pentaplast. It is a Barrier film designed to limit the transmission of $O_2$ & $CO_2$;
2. PVC with PVDC—made by K-P. It is a barrier film designed to limit $O_2$, $CO_2$ and $H_2O$; and
3. Alu—Alu—various manufacturers. It is a composite of Al and polyethylene that is heat sealable and is a barrier to virtually all gases and vapors.

All three films can be used exclusively or in combination. Most often, the plastics are used with Alu (or a composite of aluminum and paper) as a lidding stock. Alu—Alu may be used for both the receptacle and the lid.

The non-permeable packaging is specially designed for the hearing aid to minimize any entrapped air. The package is desirably designed such that the hearing aid fits snuggly into it. The small amount of $O_2$ entrapped during packaging will react with the battery chemistry, but will have minimal impact on the life of the battery.

One advantage of sealing the hearing aid in the packaging is that the user does not need to remove any tape or seal from the hearing aid. If the tape on the hearing aid is preferred, however, the packaging may be further enhanced to assist the user of the disposable aid. In one embodiment, the packaging does not block $O_2$ and the hearing aid is sealed by a non-permeable tape applied to the battery or faceplate. This tape is also attached to the packaging. When the user removes the aid from the packaging, the tape is automatically removed and retained in the packaging. In a second embodiment, the packaging has a design feature which prevents the unit from being placed in the packaging unless an electromechanical switch, such as the switch described below with reference to FIGS. 6B and 6C is in the OFF position. This prevents inadvertent degradation of the battery.

An additional degree of battery protection and storage longevity may be achieved by eliminating $O_2$ and $CO_2$ during packaging and maintaining a 50% relative humidity. It is generally known that metal-air battery life is optimized if it is maintained at approximately 50% relative humidity. Lower humidity tends to dry out the electrolyte. High humidity allows absorption of moisture and dilution of electrolyte. Accordingly, maintaining 50% RH during the storage and use life of the battery, optimizes its potential.

Thus, it may be desirable to blow an inert gas, such as nitrogen, over the hearing aid while its package is being sealed. It may also be desirable to add a small amount of water to the nitrogen to maintain the humidity level at approximately 50% after the package is sealed.

It is not generally known that a metal-air battery deprived of $O_2$ but under electrical load can deplete itself and have less than optimal energy capacity during use. In the case of a disposable hearing aid, even if non-permeable tape and/or packaging are used, if the battery is connected to the hearing aid electronics, the battery will self-discharge. Therefore, it is desirable for some type of switch to be incorporated, to separate the electrical load from the battery during storage and shipment. There are several types of switches that can be used for this purpose.

One type of switch is an ON switch that is an electrical contact, where once the hearing aid is activated it cannot be turned OFF. The simplest embodiment of this type of switch is to impose a non-conductive paper, tape or film 61 between one of the electrical contacts 76 of the signal processing circuitry 20 and the corresponding electrical contacts 77 of the battery 24, as shown in FIG. 6A. The hearing aid is manufactured with the paper or film 61 in place and extending out of the hearing aid shell 74. To activate the unit, the user pulls the tab out and allowing the contact to touch the battery, thus completing the electronic circuit. Replacing the film to turn the unit OFF is difficult, if not impossible. As described above, this tape may also be used to block the ingress of air into the battery so that, when the tape is removed, the battery is simultaneously activated and connected to the load.

A more traditional switch can also be incorporated. Non-disposable hearing aids typically have an electromechanical switch or the battery itself is used as the ON/OFF switch. Since a disposable hearing aid does not have an accessible battery, an electromechanical switch can be used. The advantage of the ON/OFF switch is that the unit can be turned OFF during storage and shipment, and in use, turned ON only when needed. Having the ability to turn OFF the unit allows the unit to be inserted and removed from the ear without feedback. Turning the unit OFF when not in use, also extends the battery life.

Another type of switch that can be incorporated is an automatic switch, which monitors the battery voltage and turns the hearing aid ON when the voltage is above some predefined value. As set forth above, in the absence of $O_2$, the metal-air batteries operate as zinc-hydroxide cells and have a lower voltage potential. During shipment and storage, the metal-air battery will have a non-permeable tape tab on it and the voltage potential, as measured under small electrical load, the voltage is less than 50% of the fully activated potential.

Figure 7:
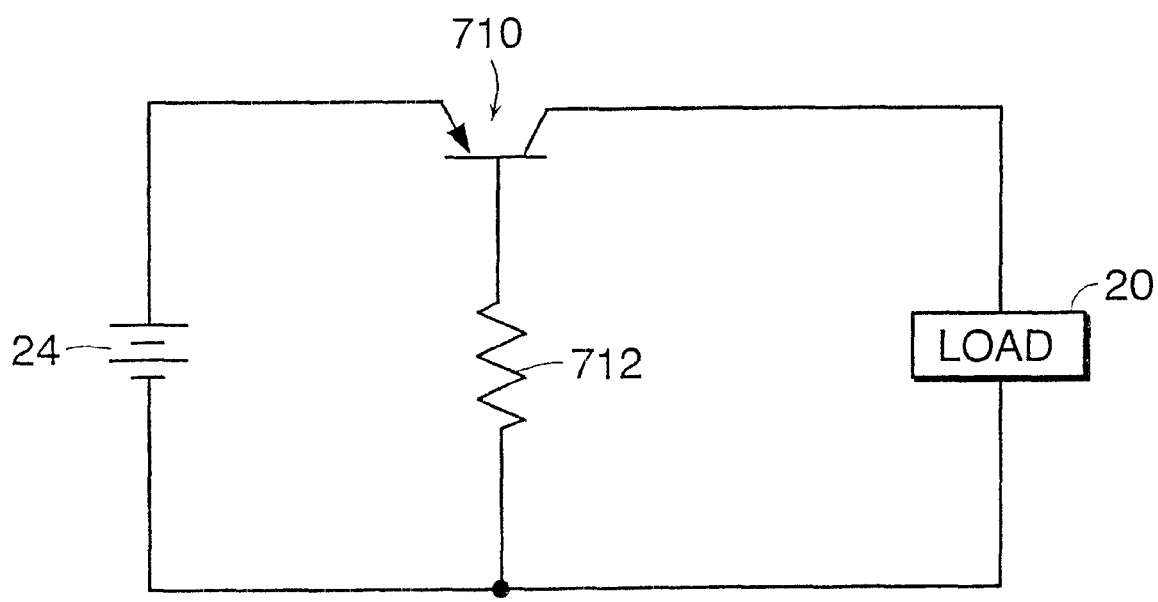
FIG. 7 illustrates a circuit for a hearing aid in accordance with one aspect of the invention.

An automatic ON only switch was previously disclosed for use with a pull tab seal on the battery of a disposable hearing aid in U.S. patent application Ser./ No. 09/124,948 and entitled "Power Source For A Hearing Aid" by Sjursen et al., which is incorporated herein by reference for its teaching on power sources for disposable hearing aids. An exemplary circuit of this type is shown in FIG. 7. The circuit includes a transistor 710 having its emitter electrode coupled to the anode of the battery 24, the collector of the transistor coupled to one terminal of the load 20 and the cathode of the battery coupled to the other terminal of the load 20. A resistor 712 connects the cathode of the battery 24 to the base of the transistor 710. When the voltage provided by the battery is less than is needed to turn on the transistor 710, the load 20 is disconnected from the battery 24. When the voltage provided by the battery exceeds the turn-on voltage for the transistor, however, the transistor 710 conducts current between its emitter and collector electrodes and power is applied to the load 20.

This circuit or a similar circuit can be incorporated into a hearing aid according to the present invention. When the hearing aid is manufactured, the battery is in a non-activated state. This is accomplished by one of the sealing means previously described. The electronic switch continuously measures the potential of the battery 24 and prevents current flow to the signal processing circuitry 20 of the hearing aid. When the unit is removed from its packaging and activated the voltage on the battery increases to its full potential. Upon sensing this voltage, the circuit passes current to the signal processing circuitry 20. The benefit of this circuit is that it eliminates the need and cost of an electromechanical switch. It also provides for a hearing aid with longer shelf life and may be easier to use as the user does not need to turn on a mechanical switch or remove a mechanical barrier to connect the hearing aid electronics to the battery.

An electronic switch, such as that disclose above, may also be used with an air block switch to reduce oxygen and moisture transfer to and from the battery when the hearing aid is not being used. FIGS. 6b and 6c show one embodiment of a disposable in-the-ear (ITE) hearing aid 10 with an air block ON/OFF switch.

Figure 6B:
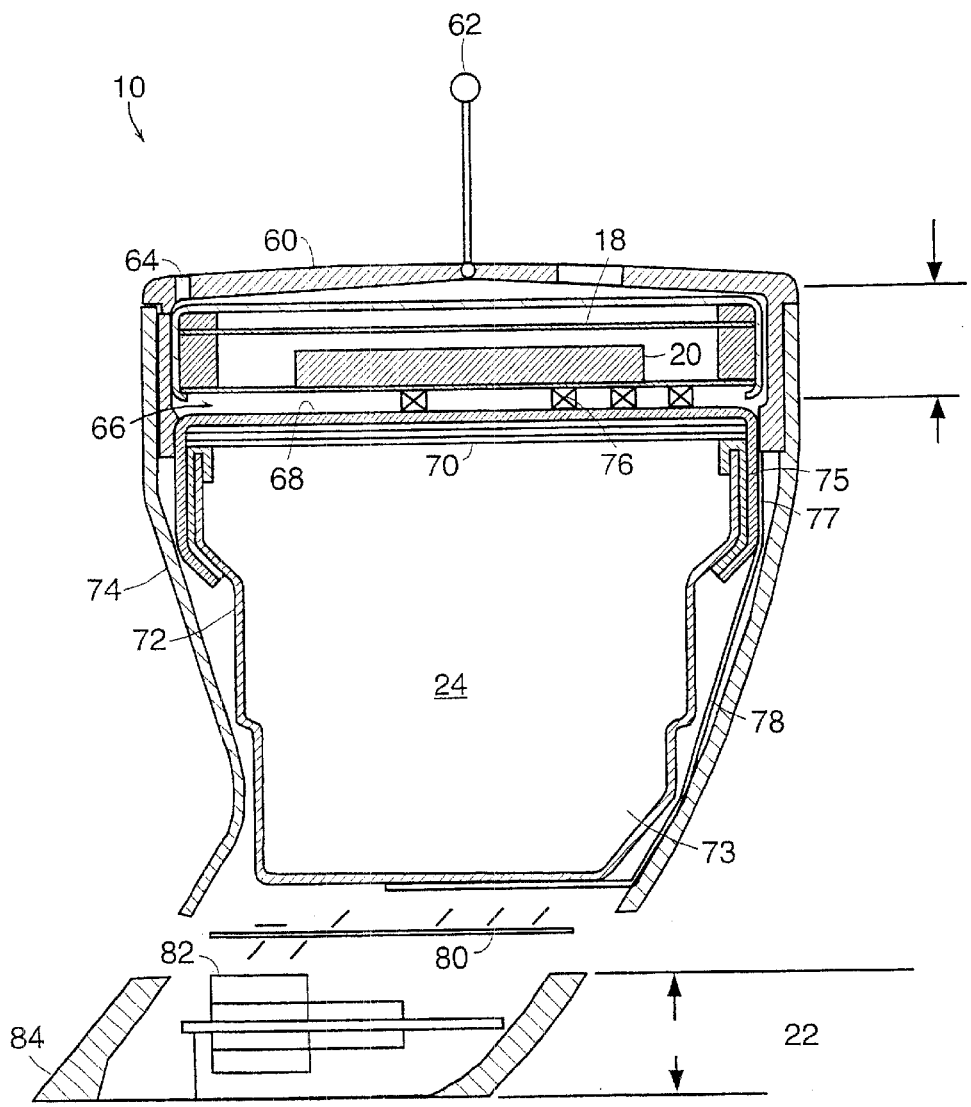
Figure 6C:
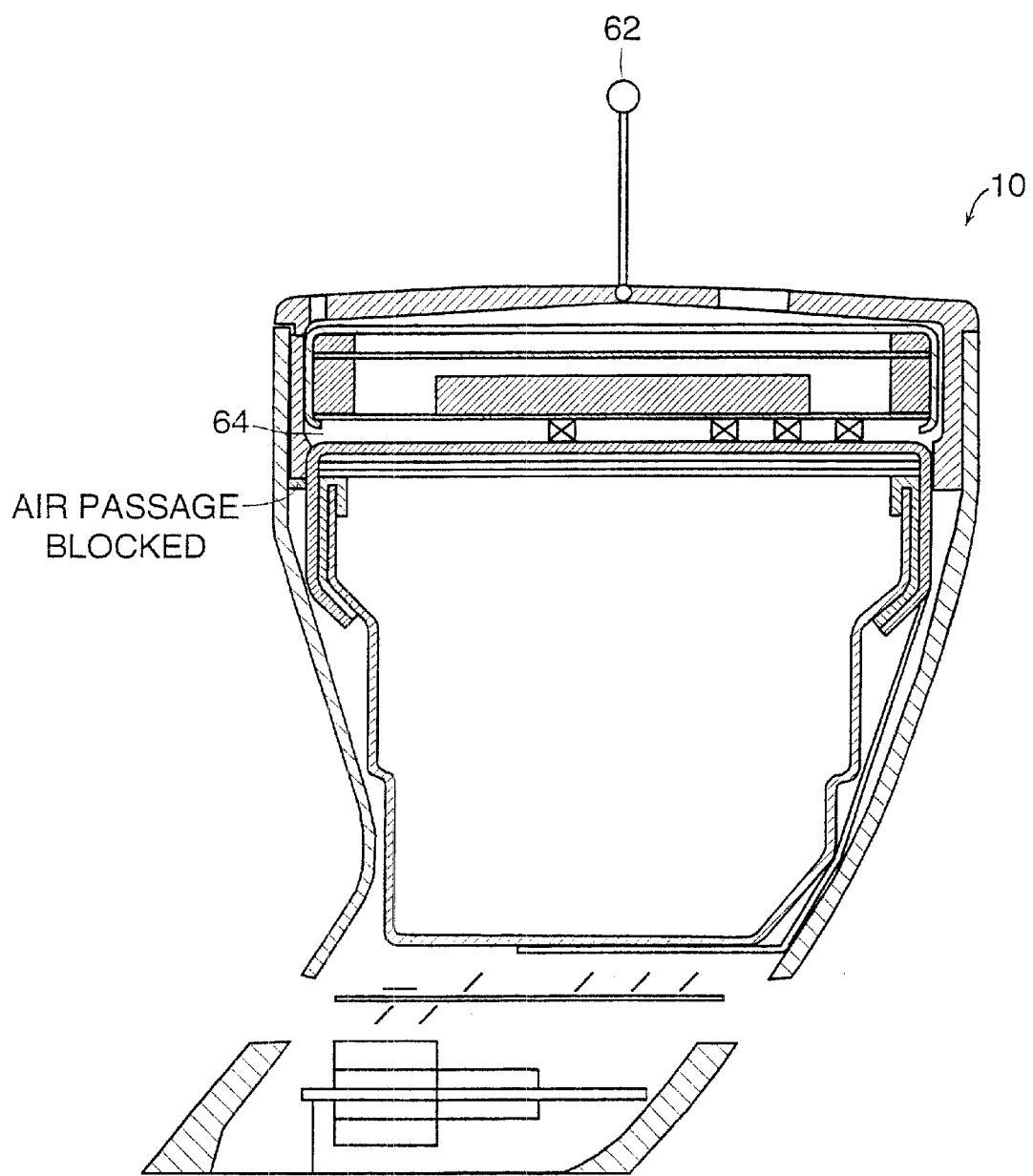

FIG. 6B shows a disposable hearing aid having a modular construction. The hearing aid includes a faceplate 60 which protects the sensitive microphone 18, anchors a pull cord 62, and provides an opening 64 through which air may pass to the battery 24. The hearing aid also includes signal processing circuitry 20 which is connected to the microphone 18, and, via electrical circuit contacts 76 to the battery 24 and a flex circuit 78. The flex circuit 78 provides a connection between the signal processing circuitry 20 and the receiver 22. In this exemplary embodiment of the invention, the receiver 22 is manufactured separately from the battery 24 and signal processing circuitry 20. The receiver is coupled to the flex circuit 78 via a spring contact interface 80 which fits between the contacts 82 of the receiver 22 and the flex circuit 78. The battery 24 and signal processing circuitry 20 are permanently mounted in a plastic case 74. The battery includes a metal wall, which is also the anode of the battery, an electrolyte mixture 73 and a cathode grid 70. The battery is enclosed by a top cap 75 which is separated from the anode 72 by an insulator 77. An opening 68 in the top cap provides air from the air channel 66 to the cathode grid 70.

The faceplate 60 is configured to slide in and out relative to the microphone 18 and hearing aid electronics 61. The plate 60 is pushed in, opening the air passage 66 when the user pushes the hearing aid into his or her ear. The faceplate 60 is pulled out, closing the air passage 66 when the user pulls the pull cord 62 to remove the hearing aid from his or her ear. When the plate 60 is pushed in, the air passage 66 is opened to allow air to enter the battery 24 via the opening 64 in the faceplate air passage 66 and battery air hole 68. When the plate 60 is pulled out, the air passage 66 is blocked as shown in FIG. 6C.

Although the disposable hearing aid has been described thus far with a metal-air type battery a hearing aid can use other types of batteries. The primary advantage of these other batteries is their higher operating voltage. As the operating voltages of the battery drop below 2 volts, the design and fabrication of audio integrated circuits becomes increasingly difficult.

The primary disadvantage of non-metal-air batteries is their reduced energy capacity. Typically, metal-air batteries have twice the capacity of non-metal-air batteries.

When a disposable hearing aid utilizes a non-metal-air battery, the issues for sealing and providing an air passageway are eliminated. Improved acoustical performance can be achieved. However, the expected usage life would be about half that of a metal-air battery.

Figure 8A:
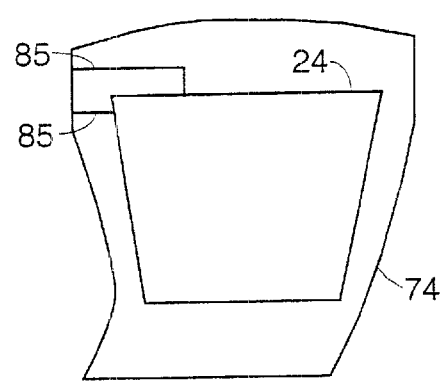
FIGS. 8a, 8b, and 8c illustrate an alternative embodiment of a hearing aid having a rechargeable type battery according to one aspect of the invention.
Figure 8B:
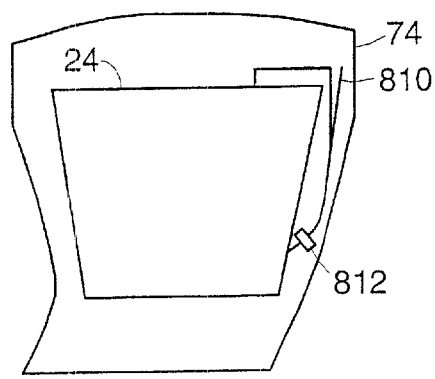
Figure 8C:
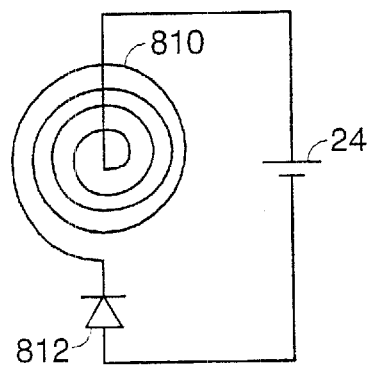

A disposable hearing aid can also utilize a rechargeable type battery as shown in FIGS. 8A and 8B. The rechargeable type battery can be sealed within the unit. However, means are added to the unit to permit external energy transfer to the battery for recharging. This can be done by providing external battery contacts 85, as shown in FIG. 8A to allow direct electrical conduction or by providing an energy transfer device, such as an inductive coil 810, as shown in FIG. 8B, or a photocell (not shown) to allow the battery to be charged from an induced alternating current (AC) or light source. In all cases, the battery would be charged when it is not in use, for example, overnight. In one possible configuration, the hearing aid may be provided with a charging unit (not shown) which provides a regulated direct current charging potential to the direct electrical contacts 85 or which provides a regulated alternating current potential to an induction coil (not shown) in the charging unit. If the hearing aid includes external battery contacts 85, then the charging of the battery is entirely under control of the charging unit. If the hearing aid is inductively coupled, however, the hearing aid may include a rectifier 812 in addition to the induction coil 810 to convert the induced AC potential into a DC potential which is applied to charge the battery 24, as shown in FIGS. 8B and 8C.

An advantage of using rechargeable batteries, is that the overall life of the unit may be extended, making it more economical. In addition, the voltage potential of rechargeable batteries may be higher than that of metal-air batteries allowing more flexibility in the design of the electronic circuitry and improved sound quality. For example, rechargeable lithium metal battery has an operating voltage of 3 volts compared with 1.3 volts for zinc air.

While this invention has been described with reference to specific embodiments, it is not necessarily limited thereto. Accordingly, the appended claims should be construed to encompass not only those forms and embodiments of the invention specifically described above, but to such other forms and embodiments as may be devised by those skilled in the art.

What is claimed is:

1. A disposable hearing aid comprising:
   a microphone which translates acoustic energy into electrical signals;
   signal processing circuitry which processes the electrical signals provided by the microphone according to a predetermined frequency response characteristic;
   a receiver which converts the processed electrical signals into acoustic energy;
   a metal-air battery contained in the hearing aid and adapted to be substantially permanently coupled to the signal processing circuitry; and
   a mechanical switch, activated by a user, to selectively deprive the battery of air or provide air to the battery contained in the hearing aid.

2. The disposable hearing aid of claim 1, further including a case which encloses the microphone, signal processing circuitry, receiver and battery, wherein:
   the case includes openings through which air is provided to the metal-air battery.

3. The hearing aid of claim 2, wherein the metal-air battery includes at least one opening through which air is allowed to enter the battery to activate the battery, the hearing aid further including a removable non-permeable seal covering the at least one opening on the battery to prevent the battery from being activated during shipment and storage of the hearing aid.

4. The disposable hearing aid of claim 3, further including electrical contacts on the signal processing circuitry which are configured to couple with corresponding contacts on the metal-air battery, and the removable non-permeable seal forms an insulating barrier between the corresponding contacts of the signal processing circuitry and the metal-air battery until the removable non-permeable seal is removed.

5. The hearing aid of claim 2, wherein:
   the metal-air battery includes openings through which air enters the battery to activate the battery; and
   the case comprises a faceplate which includes the openings through which air is provided to the battery and the case further comprises an air passageway which is configured to pneumatically couple the openings on the faceplate to the openings of the battery to provide a primary channel for providing air to the battery.

6. The hearing aid of claim 5 further including a removable seal which covers the openings on the faceplate to effectively prevent air from entering the battery.

7. The hearing aid of claim 6 wherein the removable seal which covers the openings on the faceplate of the hearing aid further includes packaging material in which the hearing aid is enclosed for shipment and storage, the removable seal being fixedly coupled to packaging material such that, when the hearing aid is removed from the packaging material, the seal is retained in the packaging material and the metal-air battery is activated.

8. The hearing aid of claim 2 further including non-permeable packaging in which the hearing aid is shipped and stored, said packaging acting to minimize the air which is provided to the metal-air battery.

9. The hearing aid of claim 8 wherein inert gas is blown over the hearing aid while the package is being sealed to reduce levels of oxygen and carbon dioxide in the sealed package.

10. The disposable hearing aid of claim 1, wherein the metal-air battery has first and second terminals and the hearing aid further comprises a switch coupled between the metal-air battery and the signal processing circuitry to selectively disconnect the signal processing circuitry from at least one of the first and second terminals of the battery.

11. The disposable hearing aid of claim 10 wherein:
    the metal-air battery exhibits a first electrical potential when the metal-air battery is deprived of air and which exhibits a second electrical potential when air is provided to the metal-air battery; and
    the switch is an electronic switch which senses the electrical potential of the battery to disconnect the at least one terminal of the battery from the signal processing circuitry when the battery exhibits the first electrical potential and to connect the at least one terminal of the battery to the signal processing circuitry when the battery exhibits the second electrical potential.

12. The hearing aid of claim 1, further including a pull string, coupled to the mechanical switch, wherein the mechanical switch is configured to provide air to the battery when a user inserts the hearing aid into the user's ear and the mechanical switch is configured to deprive the battery of air when the user pulls the pull string to remove the hearing aid from the user's ear.

13. The hearing aid of claim 10 wherein the hearing aid further includes packaging for shipping and storing the hearing aid, the packaging being configured to hold the switch in a position which prevents the switch from connecting the signal processing circuitry to the at least one terminal of the battery.

14. A disposable hearing aid comprising:
    a microphone which translates acoustic energy into electrical signals;
    signal processing circuitry which processes the electrical signals provided by the microphone according to a predetermined frequency response characteristic;
    a receiver which converts the processed electrical signals into acoustic energy;
    a non-replaceable metal-air battery coupled to the signal processing circuitry; and
    a mechanical switch, activated by a user, to selectively deprive the battery of air or provide air to the battery.

* * * * *

UNITED STATES PATENT AND TRADEMARK OFFICE
CERTIFICATE OF CORRECTION

| | | |
|---|---|---|
| PATENT NO. | : 6,473,511 B1 | Page 1 of 1 |
| APPLICATION NO. | : 09/263593 | |
| DATED | : October 29, 2002 | |
| INVENTOR(S) | : John Gregory Aceti | |

It is certified that error appears in the above-identified patent and that said Letters Patent is hereby corrected as shown below:

On the Title Page:

Replace the Related U. S. Application Data, with the following amended data:

-- (63) Continuation-in-part of application No. 08/815,852, filed on Mar. 12, 1997, now Pat. No. 5,881,159, which claims the benefit of provisional application No. 60/013,426, filed on Mar. 14, 1996. --

Column 1, lines 4-5:

Replace this paragraph with the following amended paragraph:

-- This is a continuation-in-part of application Ser. No. 08/815,852, filed on Mar. 12, 1997, now Pat. No. 5,881,159, which claims the benefit of provisional application No. 60/013,426, filed on Mar. 14, 1996. --

Signed and Sealed this

Tenth Day of July, 2007

JON W. DUDAS
*Director of the United States Patent and Trademark Office*